(12) United States Patent
Whitehurst et al.

(10) Patent No.: US 7,013,177 B1
(45) Date of Patent: Mar. 14, 2006

(54) TREATMENT OF PAIN BY BRAIN STIMULATION

(75) Inventors: Todd K. Whitehurst, Frazier Park, CA (US); Carla Mann Woods, Los Angeles, CA (US); Paul M. Meadows, Glendale, CA (US)

(73) Assignee: Advanced Bionics Corporation, Valencia, CA (US)

( * ) Notice: Subject to any disclaimer, the term of this patent is extended or adjusted under 35 U.S.C. 154(b) by 481 days.

(21) Appl. No.: 10/188,582

(22) Filed: Jul. 3, 2002

Related U.S. Application Data

(60) Provisional application No. 60/303,484, filed on Jul. 5, 2001.

(51) Int. Cl.
*A61N 1/34* (2006.01)
*A61N 1/32* (2006.01)

(52) U.S. Cl. .......................................... 607/46
(58) Field of Classification Search .................. 607/3, 607/46–47
See application file for complete search history.

(56) References Cited

U.S. PATENT DOCUMENTS

| | | | |
|---|---|---|---|
| 3,850,161 A | 11/1974 | Liss | 600/544 |
| 3,918,461 A | 11/1975 | Cooper | 607/45 |
| 4,411,258 A | 10/1983 | Pujals, Jr. | 601/134 |
| 4,646,744 A | 3/1987 | Capel | 607/58 |
| 5,193,539 A | 3/1993 | Schulman et al. | 607/61 |
| 5,193,540 A | 3/1993 | Schulman et al. | 607/61 |
| 5,312,439 A | 5/1994 | Loeb | 607/2 |
| 5,713,923 A | 2/1998 | Ward et al. | 607/13 |
| 5,938,688 A | 8/1999 | Schiff | 607/45 |
| 6,016,449 A | 1/2000 | Fischell et al. | 607/45 |
| 6,051,017 A | 4/2000 | Loeb et al. | 607/1 |
| 6,066,163 A | 5/2000 | John | 607/45 |
| 6,253,109 B1 | 6/2001 | Gielen | 607/45 |
| 6,263,225 B1 * | 7/2001 | Howard, III | 600/378 |
| 6,319,241 B1 | 11/2001 | King et al. | 604/502 |
| 6,353,762 B1 | 3/2002 | Baudino et al. | 607/45 |
| 6,366,813 B1 | 4/2002 | DiLorenzo | 607/45 |
| 6,415,184 B1 | 7/2002 | Ishikawa et al. | 607/45 |
| 6,463,328 B1 | 10/2002 | John | 607/45 |
| 6,526,318 B1 * | 2/2003 | Ansarinia | 607/46 |
| 2002/0013612 A1 * | 1/2002 | Whitehurst | 607/45 |
| 2002/0087201 A1 * | 7/2002 | Firlik et al. | 607/45 |

FOREIGN PATENT DOCUMENTS

| | | |
|---|---|---|
| WO | WO-98/37926 A1 | 2/1998 |
| WO | WO-98/43700 A1 | 3/1998 |
| WO | WO-98/43701 A1 | 3/1998 |
| WO | WO-01/60450 A1 | 2/2001 |

OTHER PUBLICATIONS

Katayama, et al., "Motor Cortex Stimulation for Post-Stroke Pain: Comparison of Spinal Cord and Thalamic Stimulation", Stereotact Funct Neurosurgery, vol. 77(1-4), (2001, pp. 183-186.

(Continued)

*Primary Examiner*—Carl Layno
(74) *Attorney, Agent, or Firm*—Laura Haburay Bishop; Bryant R. Gold

(57) ABSTRACT

Systems and methods for introducing one or more stimulating drugs and/or applying electrical stimulation to the brain to alleviate pain use at least one implantable system control unit (SCU), producing electrical pulses delivered via electrodes implanted in the brain and/or producing drug infusion pulses, wherein the stimulation is delivered to targeted areas in the brain. In some embodiments, one or more sensed conditions are used to adjust stimulation parameters.

32 Claims, 11 Drawing Sheets

OTHER PUBLICATIONS

Kumar, et al., "Deep Brain Stimulation for Intractable Pain: a 15-Year Experience", Neurosurgery, vol. 40(4), (Apr. 1997), Discussion pp. 746-747.

Mertens, et al., "Precentral Cortex Stimulation for the Treatment of Central Neuropathic Pain", Stereotactic and Functional Neurosurgery, vol. 73, (1999), pp. 122-125.

Nandi, et al., "Peri-Ventricular Grey Stimulation Versus Motor Cortex Stimulation for Post Stroke Neuropathic Paln", J Clin Neurosci, vol. 9(5), (Sep. 2002). pp. 557-561.

Peyron, et al., "Electrical Stimulation of Precentral Cortical Area in the Treatment of Central Pain: Electrophysiological and PET study", Pain, vol. 62, (1995), pp. 275-286.

Phillips, et al., "Affect of Deep Brain Stimulation on Limb paresia After Stroke", Lancet, vol. 356, No. 9225, (Jul. 15, 2000), pp. 222-223.

Saitoh, et al., "Motor Cortex Stimulation for Deafferentation Pain", Neurosurgery Focus, vol. 11(3), (Sep. 2001), pp. 1-5.

Tasker, et al., "Deep Brain Stimulation for Neuropathic Pain", Stereotact Funct Neurosurgery, vol. 65(1-4), (1995), pp. 122-124.

Tracey, et al., "Noxious Hot and Cold Stimulation Produce Common Pattens of Brain Activation in Humans: A Functional Magnetic Resonance Imaging Study", Neuroscience Letters, vol. 288(2), (Jul. 14, 2000), pp. 159-162.

Vestergaard, et al., "Lamotriglne for Central Poststroke Pain", Neurology, vol. 56, (Jan. 2001), pp. 184-189.

Talan, J., "A New 'Ahhhh' Factor / Scientists Hope Brain Electrodes Can Ease Pain and Conditions", Newsday.com, (Feb. 6, 2001), 3 pages.

Adams, et al., "Stimulation of Internal Capsule for Relief of Chronic Pain", J Neurosurgery, vol. 41(6), (Dec. 1974), pp. 740-744.

Bordi, et al., Involvement of mGluR5 on Acute Nociceptive Transmission Brain Research, vol. 871(2), (Jul. 21, 2002), pp. 223-233.

Boucher, et al., "Potent Analgesic Effects of GDNF in Neuropathic Pain States", Science, vol. 290(5489), (Oct. 6, 2000), pp. 124-127.

Brockmann, C., "Central Post Stroke Pain: a Residual Effect of Stroke", printed Jun. 2, 2003, 24 pages.

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781-790.

Carroll, et al., "Motor Cortex Stimulation for Chronic Neuropathic Pain: a Preliminary Study of 10 cases", Pain, vol. 84(2-3), (Feb. 2000), pp. 431-437.

Cooper, et al., "Reversibility of chronic neurologic deficits, Some effects of electrical stimulation of the thalamus and internal capsule in man", Appl Neurophsiol, vol. 43(3-5), (1980), pp. :244-258.

Davis, et al., "Activation of the Anterior Cingulate Cortex by Thalamic Stimulation in Patients with Chronic Pain: a Positron Emission Tomography Study", J Neurosurgery, vol. 92(1), (Jan. 2000), pp. 64-69.

Davis, et al., "Brain Targets for Pain Control", Stereotact Funct Neurosurgery, vol. 71(4), (1998), pp. 173-179.

Horn, et al., "Responses of Neurons in the Lateral Thalamus of the Cat to Stimulation of Urinary Bladder, Colon, Esophagus, and Skin", Brain Res, vol. 851(1-2), (Dec. 18, 1999), pp. 164-174.

Hosobuchi, et al., "Chronic Thalamic Stimulation for the Control of Facial Anesthesia Dolorosa", Arch Neurol, vol. 29(3), (Sep. 1973), pp. 158-161.

Hosobuchi, et al., "Chronic Thalamic and Internal Capsule Stimulation for the Control of Central Pain", Surg Neurol, vol. 4(1), (Jul. 1975), pp. 91-92.

* cited by examiner

TREATMENT OF PAIN BY BRAIN STIMULATION

The present application claims the benefit of U.S. Provisional Patent Application Ser. No. 60/303,484, filed Jul. 5, 2001, which application is incorporated herein by reference in its entirety.

FIELD OF THE INVENTION

The present invention generally relates to implantable drug delivery and electrical stimulation systems and methods, and more particularly relates to utilizing one or more implantable devices to deliver one or more stimulating drugs and/or electrical stimulation to certain areas of the brain as a treatment for pain.

BACKGROUND OF THE INVENTION

Debilitating chronic pain afflicts between 70–90 million Americans with headache (24 million), backache (23 million), arthritis (40 million), and millions more with other pathologies, diseases, and injuries. Debilitating chronic pain costs Americans over $50 billion annually, including $900 million on over the counter analgesics, and billions more in lost production.

Chronic pain consists of multiple causes and manifestations that are treated by many different healthcare practitioners. Pain can usually be linked to causes such as injury or disease but can also be idiopathic with no diagnosable origin. Pain may be characterized simplistically by the following types:

1. Nociceptive Pain

This is the common pain that signals tissue irritation, impending injury, or actual injury. Nociceptors (i.e, pain receptors) in the affected area are activated, which then transmit signals via the peripheral nerves and the spinal cord to the brain. Complex spinal reflexes (withdrawal) may be activated, followed by perception, cognitive and affective responses, and possibly voluntary action. The pain is typically perceived as related to the specific stimulus (hot, sharp, etc.) or with an aching or throbbing quality. Visceral pain is a subtype of nociceptive pain. It tends to be paroxysmal and poorly localized, as opposed to somatic pain that is more constant and well localized. Nociceptive pain is usually time limited—arthritis is a notable exception—and tends to respond well to treatment with opioids (e.g., morphine).

2. Neuropathic Pain

Neuropathic (neural injury) pain is the result of a malfunction somewhere in the nervous system. The site of the nervous system injury or malfunction can be either in the peripheral or central nervous system. The pain is often triggered by an injury, but this injury may not clearly involve the nervous system, and the pain may persist for months or years beyond the apparent healing of any damaged tissues. In this setting, pain signals no longer represent ongoing or impending injury. The pain frequently has burning, lancinating, or electric shock qualities. Persistent allodynia—pain resulting from a nonpainful stimulus, such as light touch—is also a common characteristic of neuropathic pain. Neuropathic pain is frequently chronic, and tends to have a less robust response to treatment with opioids.

3. Psychogenic Pain

Psychogenic pain describes those rare situations where it is clear that no somatic disorder is present. It is universal that psychological factors play a role in the perception and complaint of pain. These psychological factors may lead to an exaggerated or histrionic presentation of the pain problem, but even in these circumstances, it is rare that the psychological factors represent the exclusive etiology of the patient's pain.

4. Mixed Category Pain

In some conditions, the pain appears to be caused by a complex mixture of nociceptive, neuropathic and/or psychogenic factors. An initial nervous system dysfunction or injury may trigger the neural release of inflammatory mediators and subsequent neurogenic inflammation. For example, migraine headaches probably represent a mixture of neuropathic and nociceptive pain. As another example, myofascial pain is probably secondary to nociceptive input from the muscles, but the abnormal muscle activity may be the result of neuropathic conditions. Chronic pain, including chronic myofascial pain, may cause the development of ongoing representations of pain within the central nervous system that are independent of signals from the periphery. This is called the centralization or encephalization of pain.

A large variety of treatments exist for pain. However, for various reasons, many patients continue to suffer with their painful conditions. In addition, many treatments suffer from a variety of disadvantages. For instance, existing surgical procedures are highly invasive. What is needed are more and better treatment options, including systems and methods to effectively and efficiently deliver drugs directly to specific areas of the brain affecting pain, possibly in combination with electrical stimulation, to relieve pain. In combination with drug and/or electrical stimulation of specific areas of the brain affecting pain, means of sensing a patient's condition and responding with the appropriate stimulation is also needed.

BRIEF SUMMARY OF THE INVENTION

The invention disclosed and claimed herein provides treatments for pain via systems and methods for introducing one or more stimulating drugs and/or applying electrical stimulation to one or more areas of the brain. According to some embodiments of the invention, the stimulation increases excitement of one or more of those areas of the brain that exhibit chronic decreased activity in patients relative to control subjects, thereby treating or preventing pain. According to other embodiments of the invention, the stimulation decreases excitement of one or more of those areas of the brain that exhibit chronic increased activity in patients relative to control subjects, thereby treating or preventing pain.

The treatment provided by the invention may be carried out by one or more system control units (SCUs) that apply electrical stimulation and/or one or more stimulating drugs to one or more predetermined stimulation sites in the brain. In some forms of an SCU, one or more electrodes are surgically implanted to provide electrical stimulation from an implantable signal/pulse generator (IPG) and/or one or more infusion outlets and/or catheters are surgically implanted to infuse drug(s) from an implantable pump. An SCU may provide both electrical stimulation and one or more stimulating drugs when necessary and desired. In some forms of an SCU, a miniature implantable neurostimulator (a.k.a., a microstimulator), such as a Bionic Neuron (also referred to as a BION® microstimulator) or the like, is implanted substantially or entirely within the brain. The systems of the invention may also include one or more sensors for sensing symptoms or conditions that may indicate a needed treatment.

In some configurations, the SCU is implanted in a surgically-created shallow depression or opening in the skull, such as in the temporal, parietal, or frontal bone. In some such configurations, one or more electrode leads and/or catheters attached to the SCU run subcutaneously to an opening in the skull and pass through the opening into or onto the brain parenchyma and surrounding tissue. The SCUs programmed to produce electrical stimulation may provide either monopolar electrical stimulation, e.g., using the SCU case as an indifferent electrode, or to produce bipolar electrical stimulation, e.g., using one of the electrodes of an electrode array as an indifferent electrode.

The SCU used with the present invention possesses one or more of the following properties, among other properties:
- at least one pump and at least one outlet for delivering a drug or drugs to surrounding tissue and/or at least two electrodes for applying stimulating current to surrounding tissue;
- electronic and/or mechanical components encapsulated in a hermetic package made from biocompatible material(s);
- an electrical coil or other means of receiving energy and/or information inside the package, which receives power and/or data by inductive or radio-frequency (RF) coupling to a transmitting coil placed outside the body, thus avoiding the need for electrical leads to connect devices to a central implanted or external controller;
- means for receiving and/or transmitting signals via telemetry;
- means for receiving and/or storing electrical power within the SCU; and
- a form factor making the SCU implantable in a depression or opening in the skull and/or in the brain.

An SCU may operate independently, or in a coordinated manner with other implanted SCUs, other implanted devices, and/or with devices external to a patient's body. For instance, an SCU may incorporate means for sensing a patient's condition, e.g., a means for sensing pain. Sensed information may be used to control the electrical and/or drug stimulation parameters of the SCU in a closed loop manner. The sensing and stimulating means may be incorporated into a single SCU, or a sensing means may communicate sensed information to at least one SCU with stimulating means.

BRIEF DESCRIPTION OF THE DRAWINGS

The above and other aspects of the present invention will be more apparent from the following more particular description thereof, presented in conjunction with the following drawings wherein:

FIG. 3 is a parasagittal section through the mamillothalamic tract;

Corresponding reference characters indicate corresponding components throughout the several views of the drawings.

DETAILED DESCRIPTION OF THE INVENTION

Figure 1A:
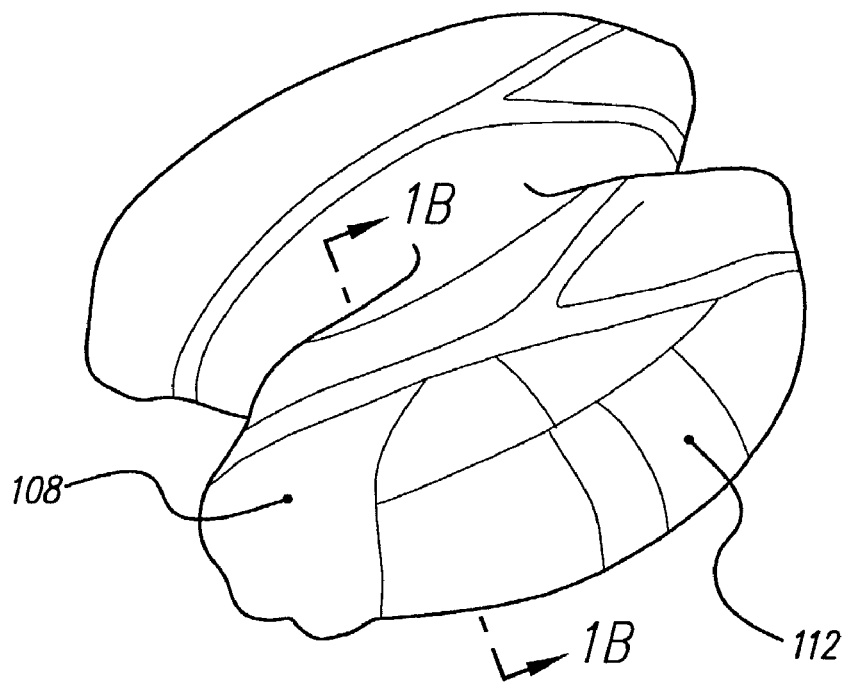
FIG. 1A is a schematic representation of the thalamus.

The following description is of the best mode presently contemplated for carrying out the invention. This description is not to be taken in a limiting sense, but is made merely for the purpose of describing the general principles of the invention. The scope of the invention should be determined with reference to the claims.

The multi-disciplinary pain treatment center is a quickly growing entity prepared to manage pain sufferers with an armamentarium of approaches including psychological rehabilitation and behavioral training, physical rehabilitation and massage therapy, chiropractic spinal manipulations, acupuncture, oral opioids and injected nerve blocking drug therapies, and surgical intervention. At least 10% of pain treated patients become intractable to these non-invasive and surgically corrective therapies.

Deep Brain Stimulation (DBS) has been pursued as a treatment for pain for the past 30 years. Peripheral pain signals are transmitted via the spinothalamic tract of the spinal cord and synapse primarily in the thalamus. Thus, the area where they synapse was seen as a prime target for DBS and was the focus of much of the early research. DBS continues to be pursued as a therapy in chronic pain patients.

Today, the pain indications that either exist or seem most promising for potential treatment by deep brain stimulation include:
Neuropathic Pain:
Complex Regional Pain Syndrome (CRPS), Type II
Steady, burning pain
Lancinating, shooting pain
Tactile hypersensitivity
Partial or complete sensory loss
Other Indicating Factors:
Failure of Spinal Cord Stimulation (SCS) (anatomic failure, not physiologic)
Topography not amenable to SCS (e.g., facial pain)
Thalamic pain syndrome (e.g., Dejerine-Roussy syndrome)
Spinal Cord Injury (SCI) (e.g., bilateral pain at all levels below spinal injury)
Psychological evaluation indicates real pain
The targets for DBS for pain typically include the following sites:
Neuropathic Pain
Medial lemniscus
Ventrobasal (VB) area of the thalamus, including the ventral posteromedial (VPM) and the ventral posterolateral (VPL) nuclei
Internal capsule
Motor cortex
Cingulate gyrus (a.k.a., cingulate cortex)
posterior complex of the thalamus (PO)
Ventrolateral nucleus of the thalamus (VL)

Nociceptive Pain:

Periventricular grey (PVG) matter and periaqueductal grey (PAG) matter, which are sometimes simply called periventricular grey and periaqueductal grey The results of DBS for pain may be varied, due to the large number of etiologies of pain, differences in the subjective patient response to pain, and different targets available for stimulation. In 1995, Tasker, et al. reported that "[p]aresthesia-producing (PP), but not periventricular grey (PVG), deep brain stimulation (DBS) proved effective in steady neuropathic pain in 25 patients receiving both, regardless of the PP site stimulated, but PVG-DBS suppressed allodynia or hyperpathia in 3 cases of stroke-induced pain. In patients with stroke-induced central pain, PP-DBS was unpleasant in 6 of 17 (35%), all with allodynia and/or hyperpathia, but not in patients with spinal cord central or peripheral neuropathic pain with allodynia or hyperpathia. Of 11 patients in whom prior ineffective dorsal column stimulation (DCS) produced appropriate paresthesia, none responded to PP-DBS; 5 of 7 did so in whom DCS produced no paresthesia or relieved pain. Periaqueductal grey DBS was nearly always unpleasant, PVG-DBS sometimes was." (Tasker RR; Vilela Filho O. "Deep brain stimulation for neuropathic pain." Stereotactic and Functional Neurosurgery, 1995;65(1–4):122-4.)

In 1997, Kumar, et al. followed 68 patients with chronic pain syndromes who underwent DBS of the periventricular gray matter, sensory thalamic nuclei, or the internal capsule. The mean age of the 54 men and 14 women in the study was 51.3 years. Indications for DBS included 43 patients with failed back syndrome, 6 with peripheral neuropathy or radiculopathy, 5 with thalamic pain, 4 with trigeminal neuropathy, 3 with traumatic spinal cord lesions, 2 with causalgic pain, 1 with phantom limb pain, and 1 with carcinoma pain. After initial screening, 53 of 68 patients (77%) elected internalization of their devices; 42 of the 53 (79%) continue to receive adequate relief of pain. Therefore, effective pain control was achieved in 42 of 68 of our initially referred patients (62%). Patients with failed back syndrome, trigeminal neuropathy, and peripheral neuropathy fared well with DBS, whereas those with thalamic pain, spinal cord injury, and postherpetic neuralgia did poorly. The authors concluded that DBS in selected patients provides long-term effective pain control with few side effects or complications. (Kumar K; Toth C; Nath RK. "Deep brain stimulation for intractable pain: a 15-year experience" Neurosurgery, 1997 April;40(4):736–46; discussion 746-7.)

Substances infused directly into the brain may also prove to be an effective treatment for chronic pain. Morphine and other opiates have a profound analgesic effect on the central nervous system. In 2000, Bordi, et al. examined the effect of the mGluR5 antagonist, MPEP (2-Methyl-6-(phenylethynyl)-pyridine), on nociceptive neurons in the ventroposterolateral (VPL) nucleus of the thalamus in response to pressure stimuli to the contralateral hindpaw of rats. Intravenous injection of MPEP blocked responses to noxious stimulation in a dose-dependent and reversible manner. MPEP action was selective to noxious stimulation because even when tested at the highest dose (10 mg/kg IV) it did not alter the responses of non-nociceptive neurons to brush stimulation. The mGluR5 antagonist did not affect nociceptive responses when applied directly to the thalamus, suggesting that thalamic receptors were not involved in this action. On the other hand, the NMDA thalamic receptors seem to be involved because the NMDA receptor antagonist, MK801, successfully blocked responses to noxious pressure stimulation following intra-thalamic injections. In the spinal cord in vitro model, MPEP (30 muM, 60 min) was also able to attenuate ventral root potentials after single shock electrical stimulation of the dorsal root and inhibit wind-up response evoked by repetitive stimulation. Taken together, these findings suggest that blockade of mGluR5 decreases nociceptive transmission in the thalamus and that these effects may be mediated by spinal cord receptors. (Bordi, Fabio; Ugolini, Annarosa. "Involvement of mGluR5 on acute nociceptive transmission" Brain Research, 871:2, 2000 Jul. 21, 223–233.)

Also in the year 2000, Boucher, et al. demonstrated that glial cell line-derived neurotrophic factor (GDNF) delivered via continuous intrathecal infusion both prevented and reversed sensory abnormalities that developed in neuropathic pain models, without affecting pain-related behavior in normal animals. GDNF appeared to work by reducing the number of damaged myelinated sensory fibers that exhibited spontaneous discharges, most likely by reversing the injury-induced changes in several sodium channel subunits. The authors concluded that these findings provided a rational basis for the use of GDNF as a therapeutic treatment for neuropathic pain states. Stephen McMahon, a co-author of the report, commented to Reuters Health, "We observed that when we discontinued treatment after several weeks, neuropathic pain re-emerged. This suggests that long-term treatment would be necessary with GDNF (or an agonist)." (Boucher T J; Okuse K; Bennett D L; Munson J B; Wood J N; McMahon S B. "Potent analgesic effects of GDNF in neuropathic pain states." Science, 2000 Oct. 6;290(5489): 124-7.)

Relatively low-frequency electrical stimulation (i.e., less than about 50–100 Hz), has been demonstrated to excite neural tissue, leading to increased neural activity. Similarly, excitatory neurotransmitters, agonists thereof, and agents that act to increase levels of an excitatory neurotransmitter (s) have been demonstrated to excite neural tissue, leading to increased neural activity. Inhibitory neurotransmitters have been demonstrated to inhibit neural tissue, leading to decreased neural activity; however, antagonists of inhibitory neurotransmitters and agents that act to decrease levels of an inhibitory neurotransmitter(s) have been demonstrated to excite neural tissue, leading to increased neural activity.

Relatively high-frequency electrical stimulation (i.e., greater than about 100–150 Hz) is believed to have an inhibitory effect on neural tissue, leading to decreased neural activity. Similarly, inhibitory neurotransmitters, agonists thereof, and agents that act to increase levels of an inhibitory neurotransmitter(s) have an inhibitory effect on neural tissue, leading to decreased neural activity. Excitatory neurotransmitters have been demonstrated to excite neural tissue, leading to increased neural activity; however, antagonists of excitatory neurotransmitters and agents that act to decrease levels of an excitatory neurotransmitter(s) inhibit neural tissue, leading to decreased neural activity.

Various electrical stimulation devices have been proposed for treating pain. Some devices stimulate through the skin, such as electrodes placed on the scalp. Other devices require significant surgical procedures for placement of electrodes, leads, and/or processing units. These devices may also require an external apparatus that needs to be strapped or otherwise affixed to the skin.

An implantable chronic stimulation device for deep brain stimulation is available from Medtronic, Inc. of Minneapolis, Minn. However, this system has several problems that make it an unacceptable option for some patients. It is not approved by the FDA for use in pain applications, so it must be used in an "off-label" manner only in the U.S. The current procedure for implantation is highly invasive, and the initial surgery for placement requires four to twelve hours. The implantable pulse generator (IPG), a major component of the system including the power source and stimulation electronics, must be implanted far from the electrodes, generally in the chest or elsewhere in the trunk of the body. The IPG is connected via a subcutaneous tunnel through the chest, neck, and head to an electrode in the brain. These systems therefore require extensive invasive surgery for implantation, and breakage of the long leads is highly likely. Additionally, the IPG is bulky, which may produce an unsightly bulge at the implant site (e.g., the chest), especially for thin patients. In addition, current implantable DBS systems use no feedback for regulation of stimulation. Finally, the system is powered by a primary battery, which may last only three to five years under normal operation. When the battery ceases to provide sufficient energy to adequately power the system, the patient must undergo an additional surgery in order to replace the IPG. The present invention provides an improved system for using one or more stimulating drugs and/or electrical stimulation to treat chronic pain, or even acute pain.

Figure 1B:
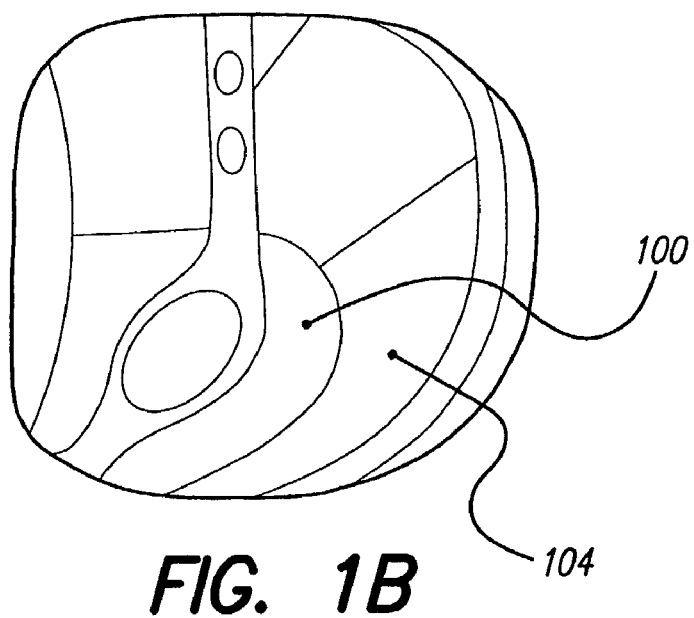
FIG. 1B is a schematic section through the thalamus of FIG. 1A.
Figure 2A:
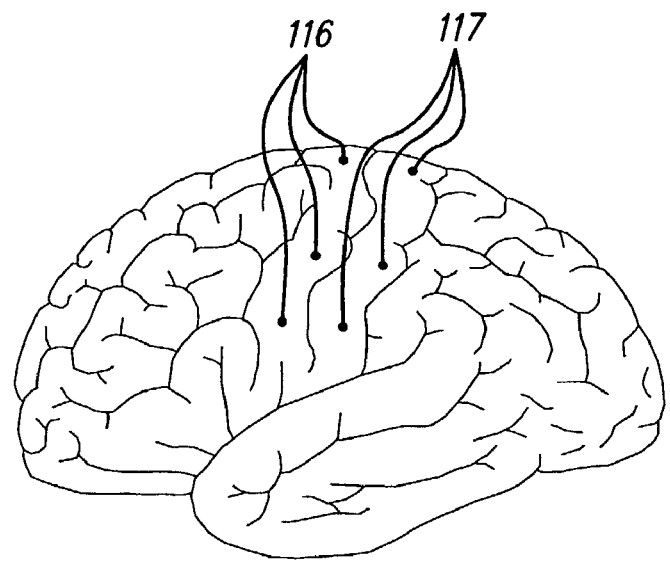
FIG. 2A is a lateral view of the cerebrum.
Figure 2B:
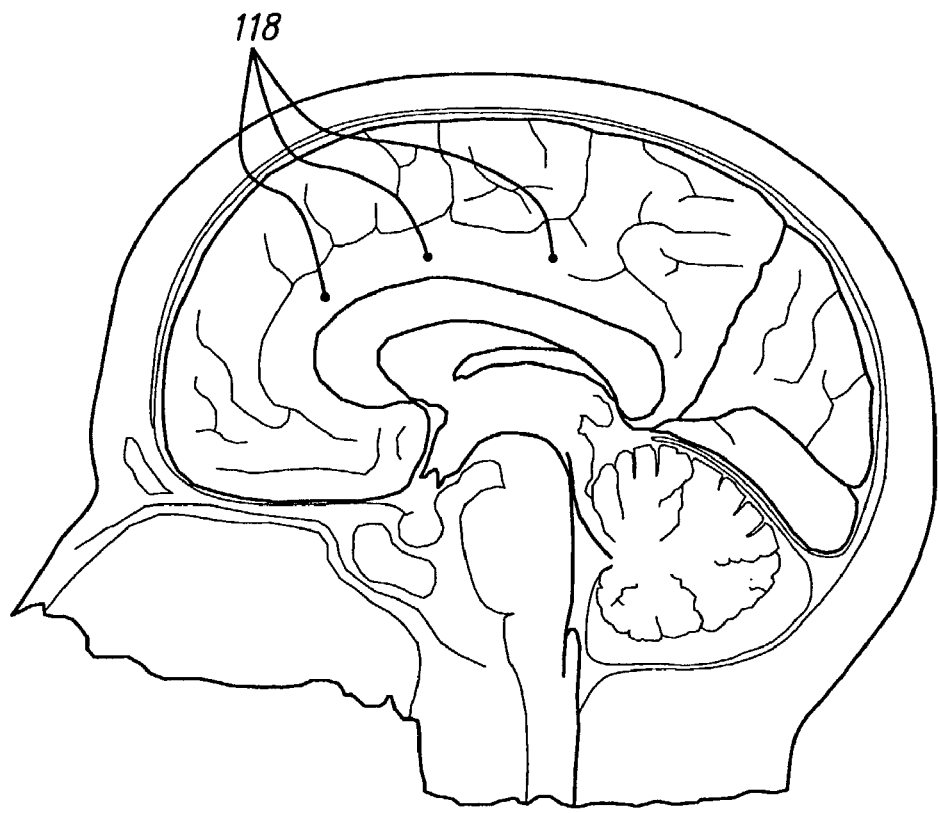
FIG. 2B is a medial view of a sagittal section of the cerebrum.
Figure 2C:
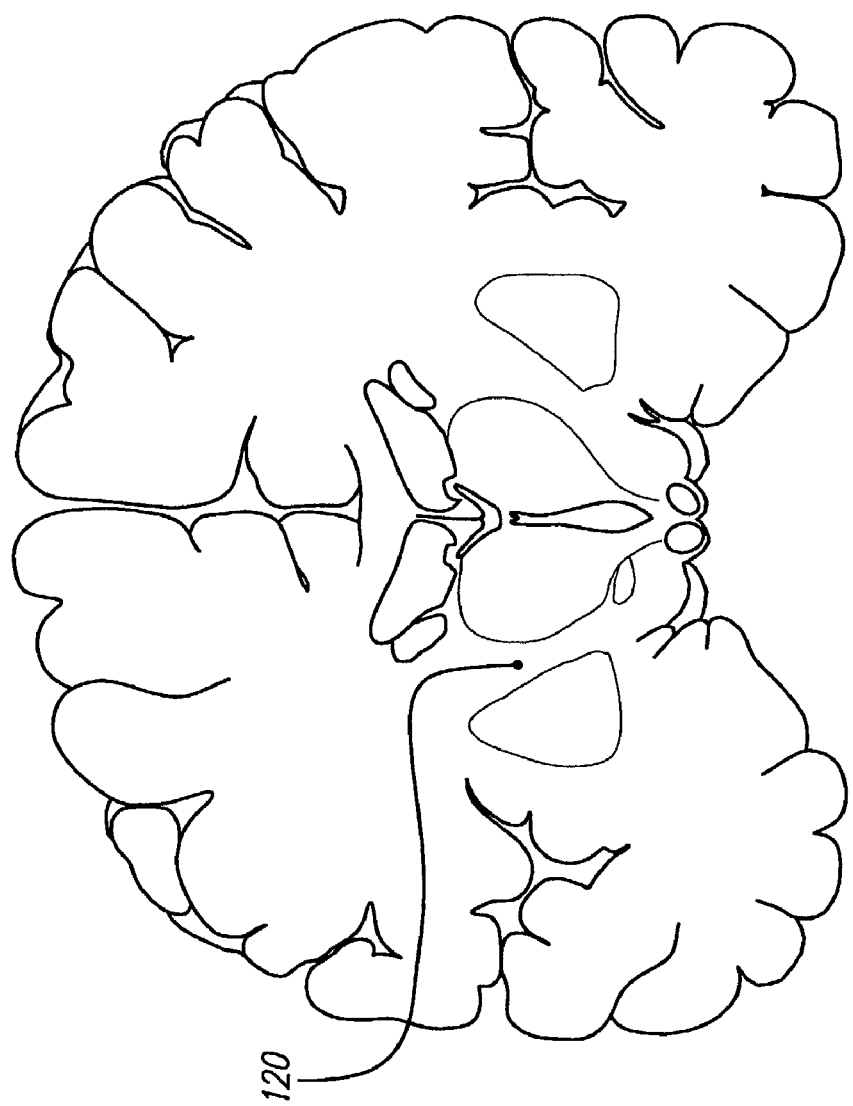
FIG. 2C is a coronal section view through the brain.
Figure 4:
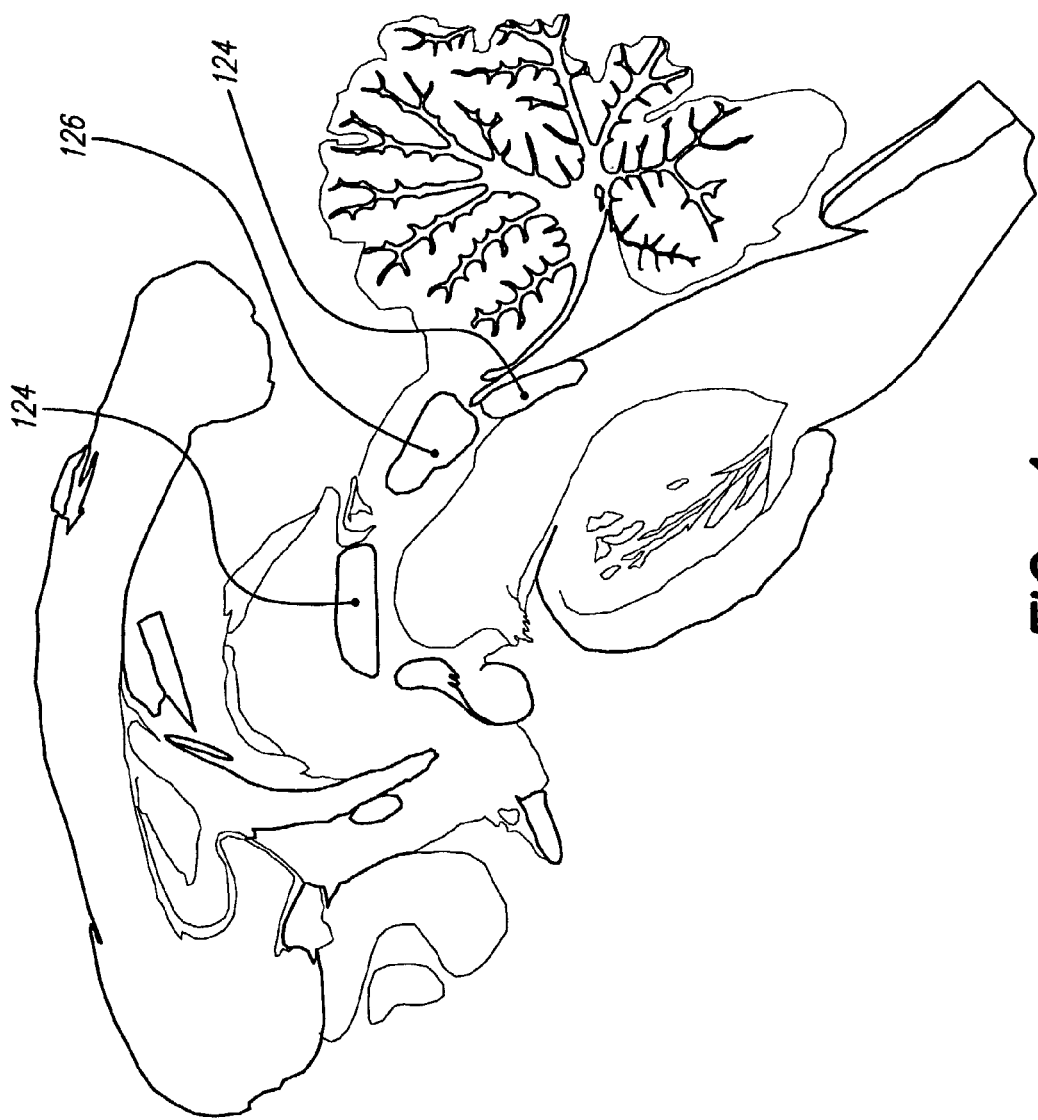
FIG. 4 is sagittal section of the cerebral hemisphere and diencephalon, brain stem, and cerebellum, close to the midline.

FIG. 1A is a schematic representation of the thalamus and FIG. 1B is a schematic section through the thalamus of FIG. 1A, showing the ventrobasal (VB) area of the thalamus, including the ventral posteromedial (VPM) nucleus 100 and the ventral posterolateral (VPL) nucleus 104. Also shown in FIG. 1A are the adjacent posterior complex of the thalamus (PO) 108 (which includes the pulvinar) and the ventrolateral nucleus of the thalamus (VL) 112. The lateral view of the cerebrum in FIG. 2A shows the motor cortex 116 (which includes the precentral gyrus) and the sensory cortex 117 (which includes the postcentral gyrus). FIG. 2B is a medial view of a sagittal section of the cerebrum, and shows the cingulate gyrus 118. A coronal section of the brain is show in FIG. 2C, and includes the internal capsule 120. FIG. 3 is a parasagittal section through the brainstem and other areas of the brain, showing the medial lemniscus 122. The sagittal section of FIG. 4, showing the cerebral hemisphere and diencephalon, brain stem, and cerebellum, includes the periventricular grey (PVG) 124 and the periaqueductal grey (PAG) 126.

As mentioned above, inhibitory stimulation may be applied to certain areas of the brain that exhibit pain-induced increased excitement. Similarly, excitatory stimulation may be applied to areas of the brain that exhibit pain-induced decreased excitement. Thus, via mechanisms described in more detail herein, the present invention provides electrical stimulation and/or stimulating drugs to these areas to adjust the level of neural activity in these areas, and thereby treat or prevent pain.

For instance, the sensory cortex 117, which essentially consists of the postcentral gyrus, receives all types of sensory input from all areas of the body. The sensations are somatotopically organized, so that stimulating one portion of the sensory cortex produces a sensation in the upper arm, while stimulating an adjacent portion may produce a sensation in the lower arm. The sensory cortex receives pain information as well as non-noxious signals, e.g., pressure and touch signals. While complete removal of the sensory cortex does not destroy the ability to perceive pain, electrical stimulation of the sensory cortex with excitatory stimulation can evoke a sensation of pain. Thus, according to the present invention and as described in more detail presently, inhibitory stimulation, via electrical and/or drug stimulation, is provided to relieve pain.

Herein, stimulating drugs comprise medications and other pharmaceutical compounds, anesthetic agents, synthetic or natural hormones, neurotransmitters, interleukins, cytokines, lymphokines, chemokines, growth factors, and other intracellular and intercellular chemical signals and messengers, and the like. Certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein may include stimulation of cell bodies and axons in the area.

According to the present invention, an implantable pump and infusion outlet(s) are used to deliver one or more stimulating drugs to specific areas of the brain and/or an implantable signal generator connected to an electrode(s) delivers electrical stimulation to specific areas in the brain. One or more electrodes are surgically implanted in the brain to provide electrical stimulation, and/or one or more infusion outlets are surgically implanted in the brain to infuse the stimulating drug(s).

Figure 5:
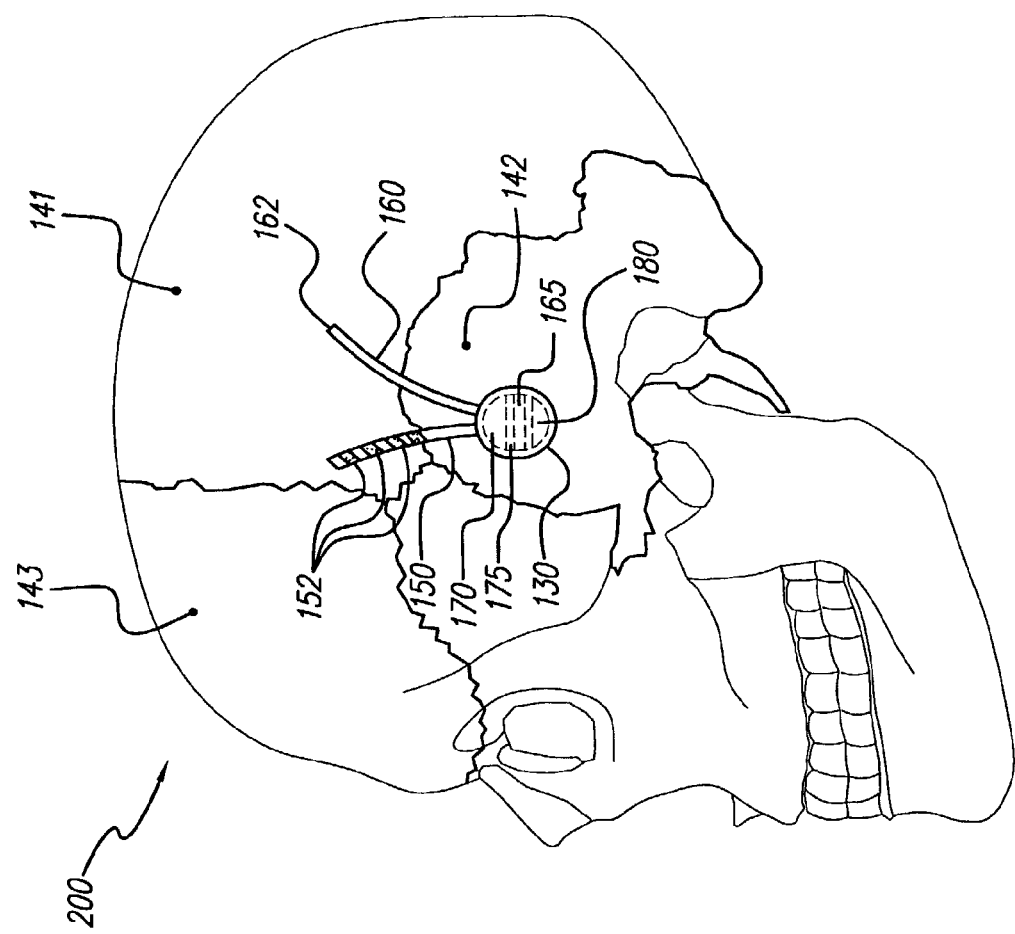
FIG. 5 illustrates a lateral view of the skull and components of some embodiments of the invention.

As depicted in FIG. 5, some embodiments of system control unit (SCU) 130 may be (but are not necessarily) implanted beneath the scalp, such as in a surgically-created shallow depression or opening in the skull of patient 200, for instance, in parietal bone 141, temporal bone 142, or frontal bone 143. SCU 130 conforms to the profile of surrounding tissue(s) and/or bone(s), and is small and compact. This may minimize pressure applied to the skin or scalp, which pressure may result in skin erosion or infection. In various embodiments, SCU 130 has a diameter of about 75 mm, or only about 65 mm, or even less than about 55 mm. In these configurations, SCU thickness (e.g., depth into the skull) may be approximately 10–12 mm, or even less than about 10 mm.

Figure 6:
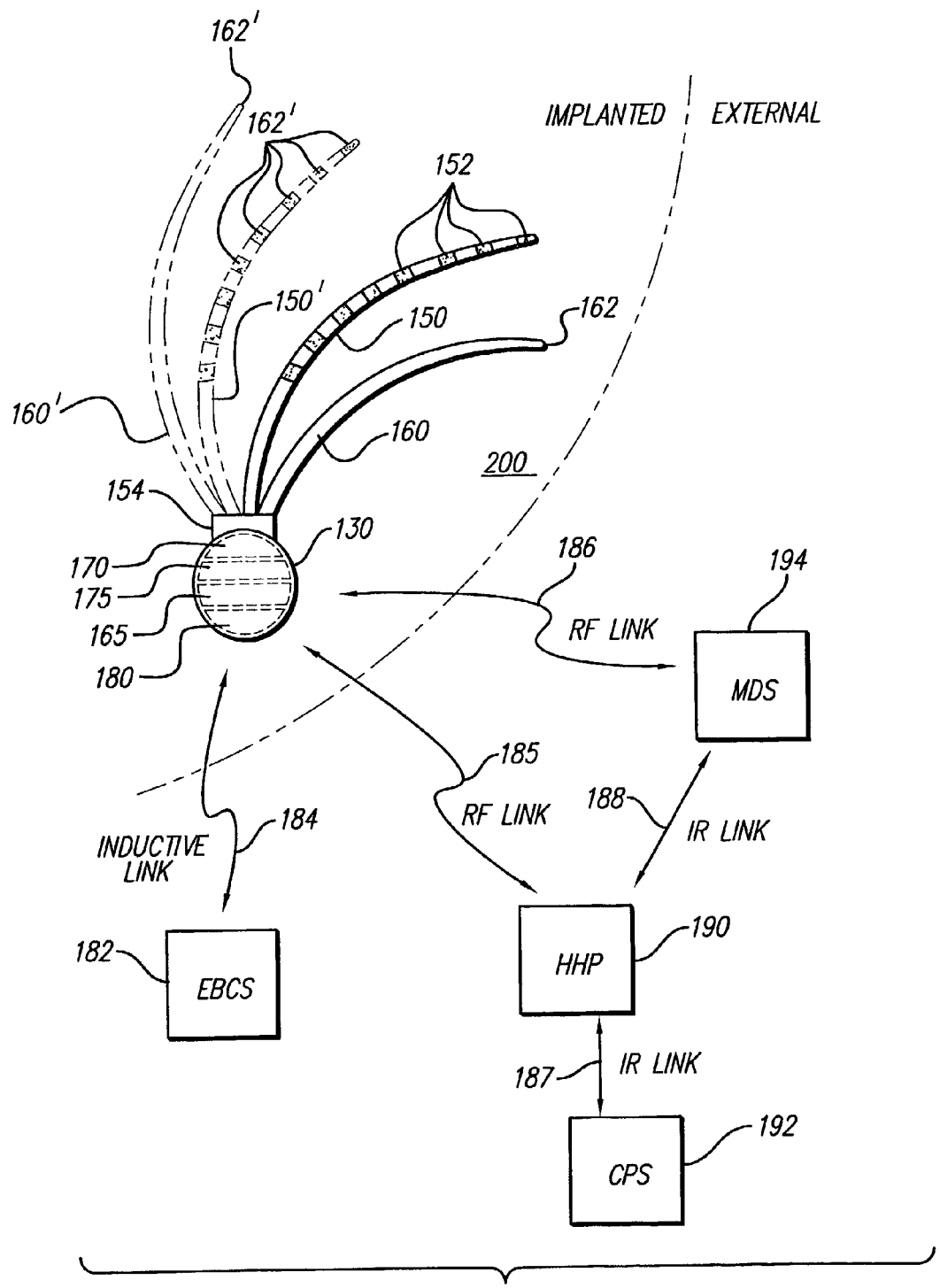
FIG. 6 illustrates internal and external components of certain embodiments of the invention.

As seen in the embodiments depicted in FIGS. 5 and 6, one or more electrode leads 150 and/or catheters 160 attached to SCU 130 run subcutaneously, for instance, in a surgically-created shallow groove(s) in the skull, to an opening(s) in the skull, and pass through the opening(s) into or onto the brain parenchyma and surrounding tissue. Recessed placement of SCU 130 and the lead(s) and/or catheter(s) may decrease the likelihood of erosion of overlying skin, and may minimize any cosmetic impact.

In embodiments such as in FIGS. 5 and 6, electrode(s) 152 are carried on lead 150 having a proximal end coupled to SCU 130. The lead contains wires electrically connecting electrodes 152 to SCU 130. SCU 130 contains electrical components 170 that produce electrical stimulation pulses that travel through the wires of lead 150 and are delivered to electrodes 152, and thus to the tissue surrounding electrodes 152. To protect the electrical components inside SCU 130, some or all of the case of the SCU may be hermetically sealed. For additional protection against, e.g., impact, the case may be made of metal (e.g. titanium) or ceramic, which materials are also, advantageously, biocompatible. In addition, SCU 130 may be configured to be Magnetic Resonance Imaging (MRI) compatible. In some alternatives, the electrical stimulation may be provided as described in International Patent Application Serial Number PCT/US01/04417 (the '417 application), filed Feb. 12, 2001, and published Aug. 23, 2001 as WO 01/60450, which application is directed to a "Deep Brain Stimulation System for the Treatment of Parkinson's Disease or Other Disorders" and is incorporated herein by reference in its entirety.

In various alternatives, stimulation is provided by one or more SCUs that are small, implantable stimulators, referred to herein as microstimulators. The microstimulators of the present invention may be similar to or of the type referred to as BION® devices (see FIGS. 7A, 7B, and 7C). The following documents describe various details associated with the manufacture, operation and use of BION implantable microstimulators, and are all incorporated herein by reference:

| Application/ Patent/ Publication No. | Filing/Publication Date | Title |
|---|---|---|
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| U.S. Pat. No. 5,324,316 | Issued Jun. 28, 1994 | Implantable Microstimulator |
| U.S. Pat. No. 5,405,367 | Issued Apr. 11, 1995 | Structure and Method of Manufacture of an Implantable Microstimulator |
| PCT Publication WO 98/37926 | Published Sep. 3, 1998 | Battery-Powered Patient Implantable Device |
| PCT Publication WO 98/43700 | Published Oct. 8, 1998 | System of Implantable Devices For Monitoring and/or Affecting Body Parameters |
| PCT Publication WO 98/43701 | Published Oct. 8, 1998 | System of Implantable Devices For Monitoring and/or Affecting Body Parameters |
| U.S. Pat. No. 6,051,017 | Issued Apr. 18, 2000 | Improved Implantable Microstimulator and Systems Employing Same |
|  | Published September 1997 | Micromodular Implants to Provide Electrical Stimulation of Paralyzed Muscles and Limbs, by Cameron, et al., published in IEEE Transactions on Biomedical Engineering, Vol. 44, No. 9, pages 781–790. |

Figure 7A:
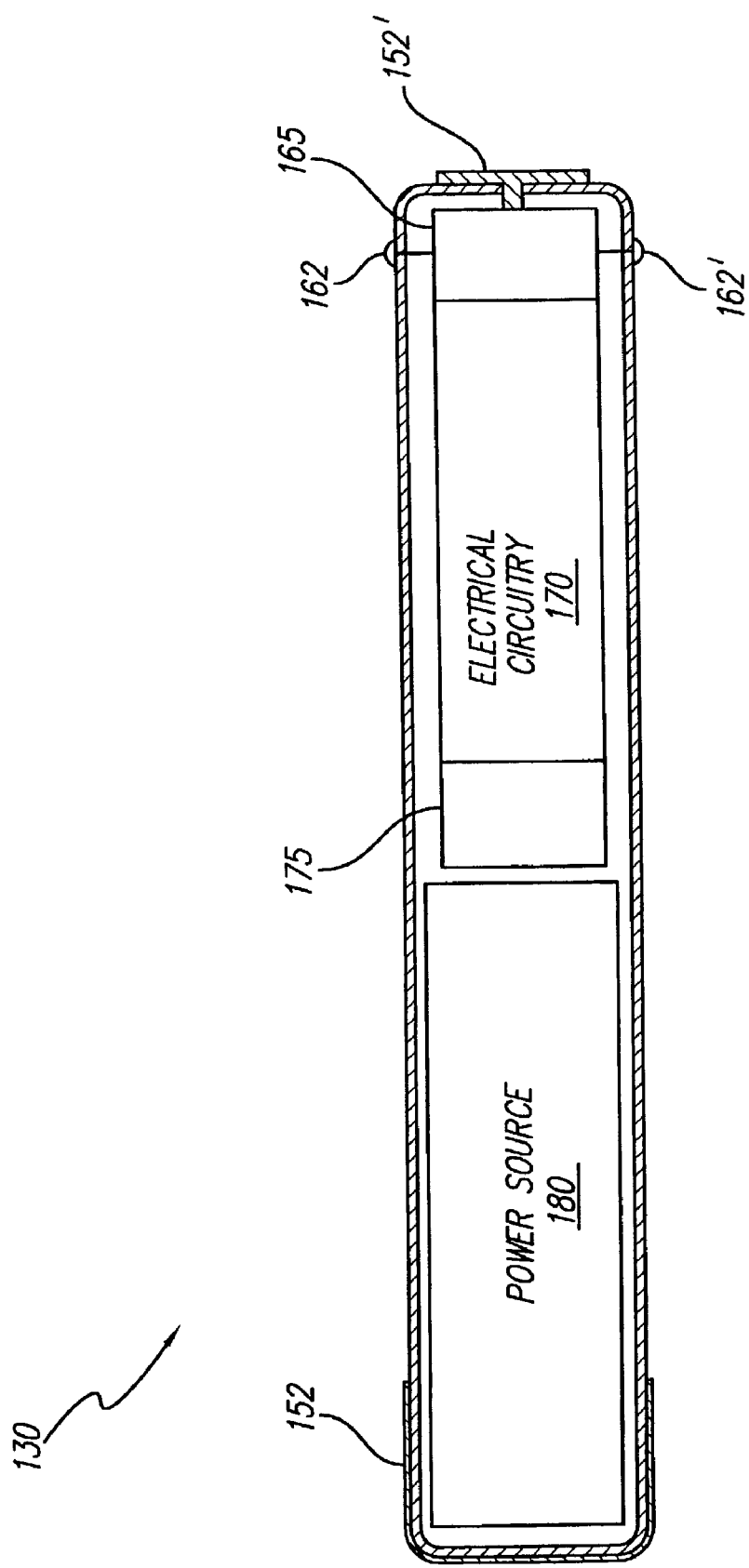
FIGS. 7A, 7B, and 7C show some of the possible configurations of an implantable microstimulator of the present invention.
Figure 7B:
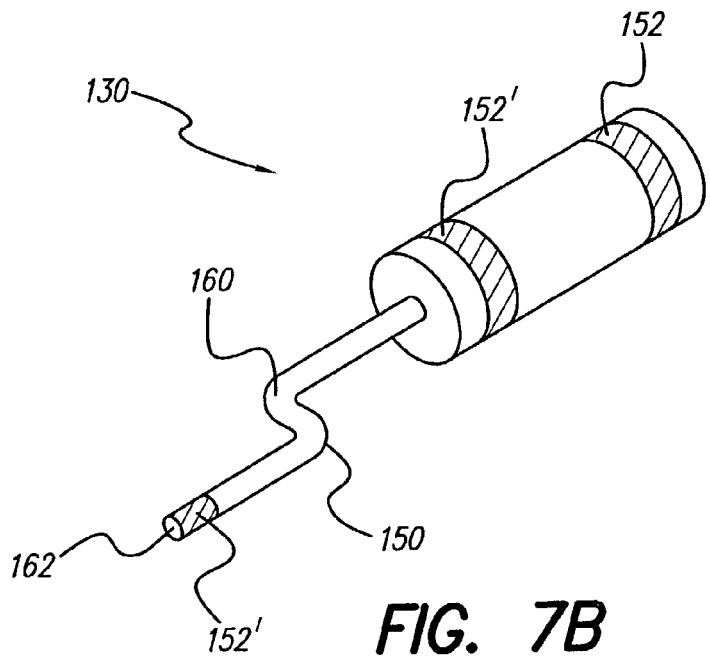
Figure 7C:
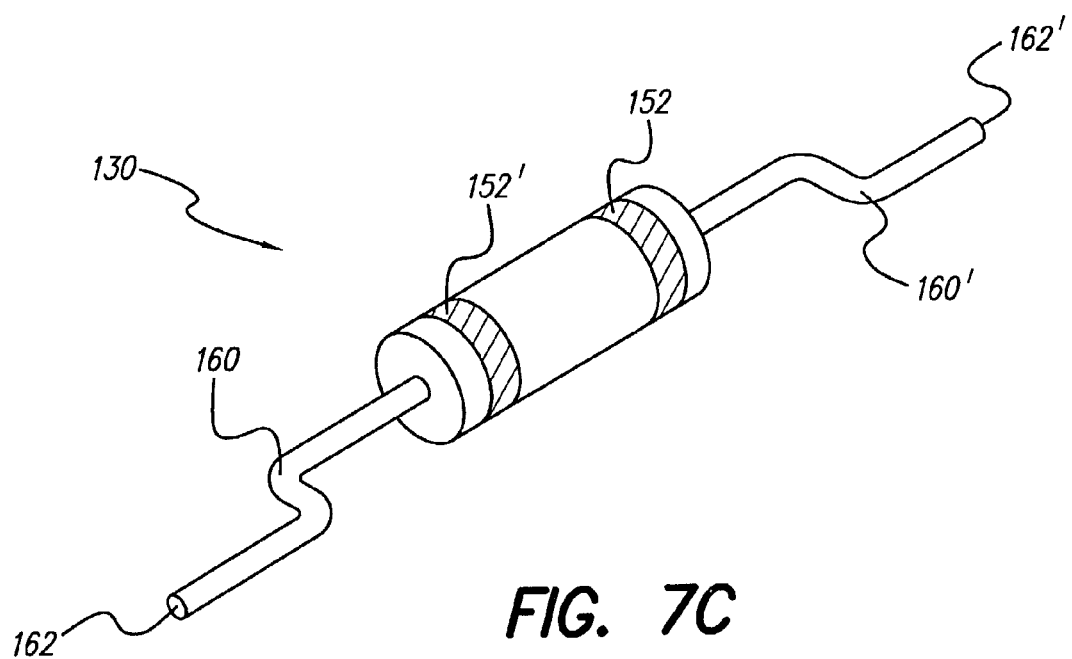

As shown in FIGS. 7A, 7B, and 7C, microstimulator SCUs 130 may include a narrow, elongated capsule containing electronic circuitry 170 connected to electrodes 152 and 152', which may pass through the walls of the capsule at either end. Alternatively, electrodes 152 and/or 152' may be built into the case and/or arranged on a catheter 160 (FIG. 7B) or on a lead, as described below. As detailed in the referenced publications, electrodes 152 and 152' generally comprise a stimulating electrode (to be placed close to the target tissue) and an indifferent electrode (for completing the circuit). Other configurations of microstimulator SCU 130 are possible, as is evident from the above-referenced publications, and as described in more detail herein.

Certain configurations of implantable microstimulator SCU 130 are sufficiently small to permit placement in or adjacent to the structures to be stimulated. For instance, in these configurations, SCU 130 may have a diameter of about 4–5 mm, or only about 3 mm, or even less than about 3 mm. In these configurations, SCU length may be about 25–35 mm, or only about 20–25 mm, or even less than about 20 mm. The shape of the microstimulator may be determined by the structure of the desired target, the surrounding area, and the method of implantation. A thin, elongated cylinder with electrodes at the ends, as shown in FIGS. 7A, 7B, and 7C, is one possible configuration, but other shapes, such as cylinders, disks, spheres, and helical structures, are possible, as are additional electrodes, infusion outlets, leads, and/or catheters.

The microstimulator, when certain configurations are used, may be implanted with a surgical tool such as a tool specially designed for the purpose, or with a hypodermic needle, or the like. Alternatively, the device may be implanted via conventional surgical methods (e.g., via a small incision), or may be placed using endoscopic or laparoscopic techniques. A more complicated surgical procedure may be required for sufficient access to certain tissues, or for fixing the microstimulator in place.

Deep brain stimulation (DBS) electrodes are typically targeted and implanted with the guidance of a stereotactic frame. The diameter of DBS electrodes is typically 1.5 mm or less. Microstimulator SCU 130 may be implanted with the aid of a stereotactic frame/tools via a minimal surgical procedure (e.g., through a small bur hole) adjacent to or in the sites that have demonstrated efficacy in the treatment of pain, e.g., the ventrobasal (VB) area of the thalamus, including the ventral posteromedial (VPM) nucleus and the ventral posterolateral (VPL) nucleus, the posterior complex of the thalamus (PO), and/or the ventrolateral nucleus of the thalamus (VL), among other locations. As mentioned earlier, microstimulator SCU 130 may have a diameter of about 3 mm or less, allowing it to fit through a conventional bur hole in the skull. Instead of or in addition to stereotactic techniques, microstimulator SCU 130 may be implanted with the aid of other techniques, e.g., CT or ultrasound image guidance. However, even with such techniques, microstimulator SCU 130 itself requires only a relatively small hole in the skull for implantation, i.e., a hole as large as the diameter of the implanted device.

The external surfaces of microstimulator SCU 130 may advantageously be composed of biocompatible materials. SCU capsule may be made of, for instance, glass, ceramic, or other material that provides a hermetic package that will exclude water vapor but permit passage of electromagnetic fields used to transmit data and/or power. Electrodes 152 and 152' may be made of a noble or refractory metal or compound, such as platinum, iridium, tantalum, titanium, titanium nitride, niobium or alloys of any of these, in order to avoid corrosion or electrolysis which could damage the surrounding tissues and the device.

In certain embodiments of the instant invention, microstimulator SCU 130 comprises two, leadless electrodes. However, either or both electrodes 152 and 152' may alternatively be located at the ends of short, flexible leads as described in U.S. patent application Ser. No. 09/624,130, filed Jul. 24, 2000, which is incorporated herein by reference in its entirety. The use of such leads permits, among other things, electrical stimulation to be directed more locally to targeted tissue(s) a short distance from the surgical fixation of the bulk of microstimulator SCU 130, while allowing most elements of the microstimulator to be located in a more surgically convenient site. This minimizes the distance traversed and the surgical planes crossed by the device and any lead(s). In most uses of this invention, the leads are no longer than about 150 mm.

As mentioned earlier, stimulation is provided in accordance with the teachings of the present invention by electrical stimulation and/or one or more stimulating drugs delivered to the body by one or more system control units (SCUs). In the case of electrical stimulation only, SCUs include a microstimulator and/or an implantable pulse/signal generator (IPG), or the like. In the case of drug infusion only, an SCU comprises an implantable pump or the like. In cases requiring both electrical stimulation and drug infusion, more than one SCU may be used. Alternatively, when needed and/or desired, an SCU provides both electrical stimulation and one or more stimulating drugs.

In the case of treatment alternatively or additionally constituting drug infusion, SCU 130 (which herein refers to IPGs, implantable pumps, IPG/pump combinations, microstimulators for drug and/or electrical stimulation, and/or other alternative devices described herein) may contain at least one pump 165 for storing and dispensing one or more drugs through outlet(s) 162/162' and/or catheter(s) 160/160' into a predetermined site(s) in the brain tissue. When a catheter is used, it includes at least one infusion outlet 162, usually positioned at least at a distal end, while a proximal end of the catheter is connected to SCU 130.

According to some embodiments of the invention, such as described in the previously referenced '417 application and as depicted in FIG. 6, at least one lead 150 is attached to SCU 130, via a suitable connector 154, it necessary. Each lead includes at least two electrodes 152, and may include as many as sixteen or more electrodes 152. Additional leads 150' and/or catheter(s) 160' may be attached to SCU 130. Hence, FIG. 6 shows (in phantom lines) a second catheter 160', and a second lead 150', having electrodes 152' thereon, also attached to SCU 130. Similarly, the SCUs 130 of FIGS. 7A, 7B, and 7C have outlets 162, 162' for infusing a stimulating drug(s) and electrodes 152, 152' for applying electrical stimulation.

Lead(s) 150/150' of certain embodiments of the present invention may be less than about 5 mm in diameter, or even less than about 1.5 mm in diameter. Electrodes 152, 152' on leads 150, 150' may be arranged as an array, for instance, as two or more collinear electrodes, or even as four or more collinear electrodes, or they may not be collinear. A tip electrode may also be supplied at the distal end of one or more leads.

In some embodiments, SCU 130 is programmable to produce either monopolar electrical stimulation, e.g., using the SCU case as an indifferent electrode, or bipolar electrical stimulation, e.g., using one of the electrodes of the electrode array as an indifferent electrode. Some embodiments of SCU 130 have at least four channels and drive up to sixteen electrodes or more.

SCU 130 contains, when necessary and/or desired, electronic circuitry 170 for receiving data and/or power from outside the body by inductive, radio frequency (RF), or other electromagnetic coupling. In some embodiments, electronic circuitry 170 includes an inductive coil for receiving and transmitting RF data and/or power, an integrated circuit (IC) chip for decoding and storing stimulation parameters and generating stimulation pulses (either intermittent or continuous), and additional discrete electronic components required to complete the electronic circuit functions, e.g., capacitor(s), resistor(s), coil(s), and the like.

SCU 130 also includes, when necessary and/or desired, a programmable memory 175 for storing a set(s) of data, stimulation, and control parameters. Among other things, memory 175 may allow electrical and/or drug stimulation to be adjusted to settings that are safe and efficacious with minimal discomfort for each individual. Specific parameters may provide therapeutic advantages for various severities, locations, and types of pain. For instance, some patients may respond favorably to intermittent stimulation, while others may require continuous treatment for relief. In some embodiments, electrical and drug stimulation parameters are controlled independently, e.g., continuous drug stimulation and no electrical stimulation. However, in some instances, they may advantageously be coupled, e.g., electrical stimulation may be programmed to occur only during drug infusion.

In addition, different stimulation parameters may have different effects on neural tissue. Therefore, parameters may be chosen to target specific neural populations and/or to exclude others, or to increase neural activity in specific neural populations and/or to decrease neural activity in others. For example, relatively low frequency neurostimulation (i.e., less than about 50–100 Hz) typically has an excitatory effect on surrounding neural tissue, leading to increased neural activity, whereas relatively high frequency neurostimulation (i.e., greater than about 100–150 Hz) may have an inhibitory effect, leading to decreased neural activity. Similarly, excitatory neurotransmitters (e.g., norepinephrine, epinephrine, glutamate, acetylcholine, serotonin, dopamine), agonists thereof, and agents that act to increase levels of an excitatory neurotransmitter(s) (e.g., edrophonium, Mestinon) generally have an excitatory effect on neural tissue, while inhibitory neurotransmitters (e.g., dopamine, glycine, and gamma-aminobutyric acid, a.k.a. GABA), agonists thereof, and agents that act to increase levels of an inhibitory neurotransmitter(s) generally have an inhibitory effect. (Dopamine acts as an excitatory neurotransmitter in some locations and circumstances, and as an inhibitory neurotransmitter in other locations and circumstances.) However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g. prazosin, metoprolol) and agents that decrease levels of excitatory neurotransmitter(s) may inhibit neural activity.

Some embodiments of SCU 130 also include a power source and/or power storage device 180. Possible power options for a stimulation device of the present invention, described in more detail below, include but are not limited to an external power source coupled to the stimulation device (e.g., via an RF link), a self-contained power source utilizing any suitable means of generation or storage of energy (e.g., a primary battery, a replenishable or rechargeable battery such as a lithium ion battery, an electrolytic capacitor, a super- or ultra-capacitor, or the like), and if the self-contained power source is replenishable or rechargeable, means of replenishing or recharging the power source (e.g., an RF link, an optical link, a thermal link, or other energy-coupling link).

In embodiments such as shown in FIG. 6, SCU 130 includes a rechargeable battery as a power source/storage device 180. The battery may be recharged, as required, from an external battery charging system (EBCS) 182, typically through an inductive link 184. In these embodiments, and as explained more fully in the earlier referenced '417 PCT application, SCU 130 includes a processor and other electronic circuitry 170 that allow it to generate stimulation pulses that are applied to the patient 200 through electrodes 152 and/or outlet(s) 162 in accordance with a program and stimulation parameters stored in programmable memory 175. Stimulation pulses of drugs include various types and/or rates of infusion, such as intermittent infusion, infusion at a constant rate, and bolus infusion.

According to certain embodiments of the invention, an SCU operates independently. According to various embodiments of the invention, an SCU operates in a coordinated manner with other SCU(s), other implanted device(s), and/or other device(s) external to the patient's body. For instance, an SCU may control or operate under the control of another implanted SCU(s), other implanted device(s), and/or other device(s) external to the patient's body. An SCU may communicate with other implanted SCUs, other implanted devices, and/or devices external to a patient's body via, e.g., an RF link, an ultrasonic link, a thermal link, and/or an optical link. Specifically, an SCU may communicate with an external remote control (e.g., patient and/or physician programmer) that is capable of sending commands and/or data to an SCU and that may also be capable of receiving commands and/or data from an SCU.

For example, some embodiments of SCU 130 of the present invention may be activated and deactivated, programmed and tested through a hand held programmer (HHP) 190 (which may also be referred to as a patient programmer and may be, but is not necessarily, hand held), a clinician programming system (CPS) 192 (which may also be hand held), and/or a manufacturing and diagnostic system (MDS) 194 (which may also be hand held). HHP 190 may be coupled to SCU 130 via an RF link 185. Similarly, MDS 194 may be coupled to SCU 130 via another RF link 186. In a like manner, CPS 192 may be coupled to HHP 190 via an infra-red link 187; and MDS 194 may be coupled to HHP 190 via another infra-red link 188. Other types of telecommunicative links, other than RF or infra-red may also be used for this purpose. Through these links, CPS 192, for example, may be coupled through HHP 190 to SCU 130 for programming or diagnostic purposes. MDS 194 may also be coupled to SCU 130, either directly through RF link 186, or indirectly through IR link 188, HHP 190, and RF link 185.

Figure 8:
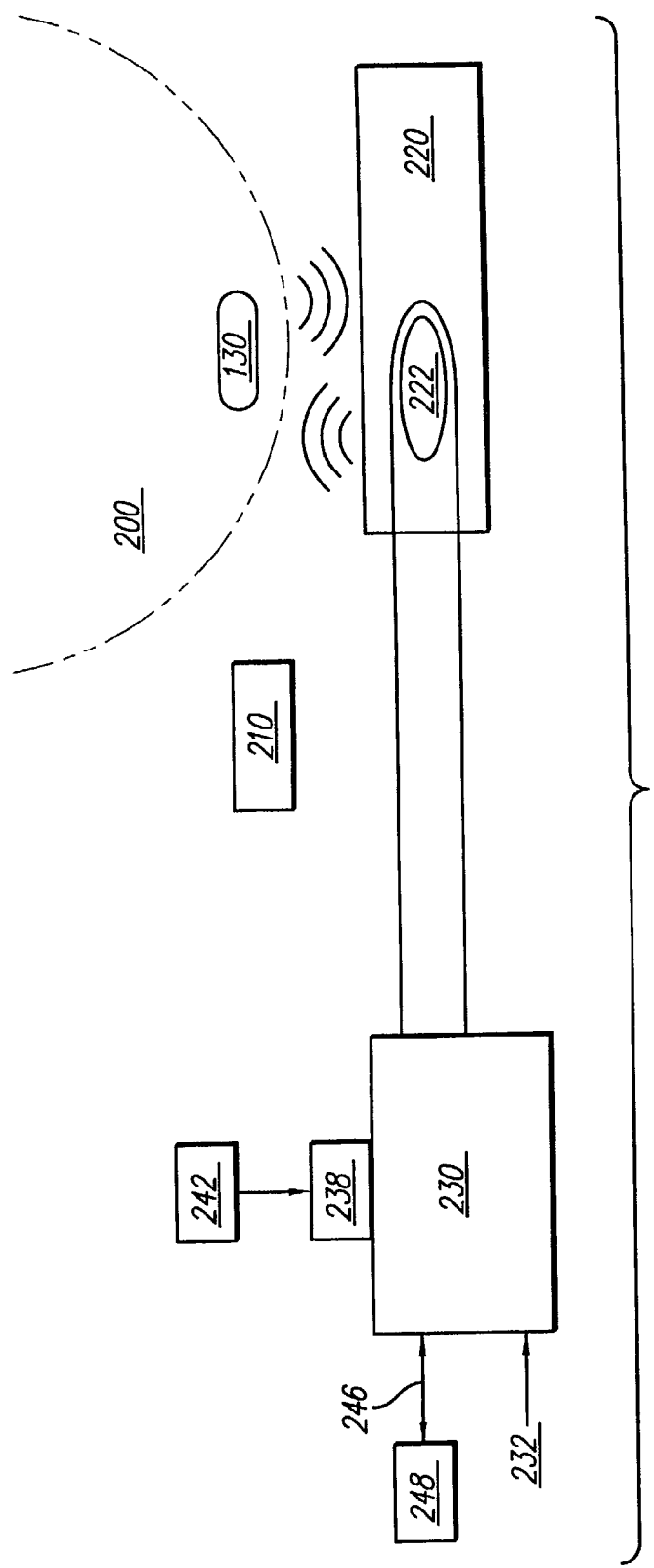
FIG. 8 illustrates external components of various embodiments of the invention.

In certain embodiments, using for example, a BION microstimulator(s) as described in the above referenced patents, and as illustrated in FIG. 8, the patient 200 switches SCU 130 on and off by use of controller 210, which may be handheld. SCU 130 is operated by controller 210 by any of various means, including sensing the proximity of a permanent magnet located in controller 210, sensing RF transmissions from controller 210, or the like.

External components for programming and/or providing power to various embodiments of SCU 130 are also illustrated in FIG. 8. When communication with such an SCU 130 is desired, patient 200 is positioned on or near external appliance 220, which appliance contains one or more inductive coils 222 or other means of communication (e.g., RF transmitter and receiver). External appliance 220 is connected to or is a part of external electronic circuitry appliance 230 which may receive power 232 from a conventional power source. External appliance 230 contains manual input means 238, e.g., a keypad, whereby the patient 200 or a caregiver 242 may request changes in electrical and/or drug stimulation parameters produced during the normal operation of SCU 130. In these embodiments, manual input means 238 includes various electromechanical switches and/or visual display devices that provide the patient and/or caregiver with information about the status and prior programming of SCU 130.

Alternatively or additionally, external electronic appliance 230 is provided with an electronic interface means 246 for interacting with other computing means 248, such as by a serial interface cable or infrared link to a personal computer or to a telephone modem or the like. Such interface means 246 may permit a clinician to monitor the status of the implant and prescribe new stimulation parameters from a remote location.

The external appliance(s) may be embedded in a cushion, pillow, or hat. Other possibilities exist, including a head band, patch, or other structure(s) that may be affixed to the patient's body or clothing. External appliances may include a package that can be, for instance, worn on the belt, may include an extension to a transmission coil affixed, for example, with a velcro band or adhesive, or may be combinations of these or other structures able to perform the functions described herein.

In order to help determine the strength and/or duration of electrical stimulation and/or the amount and/or type(s) of stimulating drug(s) required to produce the desired effect, in some embodiments, a patient's response to and/or need for treatment is sensed. For example, electrical activity of the brain (e.g., EEG or discharge frequency of a neural population) may be sensed.

For instance, one or more electrodes may be used for recording electrical signals from the brain. Recording of the neural activity of one or more areas being stimulated, e.g., the ventrobasal area of the thalamus, may be performed in order to determine the discharge frequency of the neural population. This sensing may occur during stimulation or during a temporary suspension of stimulation. The amplitude of stimulation is increased if the discharge frequency is above a programmable threshold frequency, and the amplitude of stimulation is decreased if the discharge frequency is less than another programmable threshold frequency. The two programmable threshold frequencies may be the same or may be different in order to achieve hysteresis.

Other measures of the state of the patient may additionally or alternatively be sensed. For instance, neurotransmitter levels, their associated breakdown product levels, hormone levels, or other substances, such as dopamine levels, interleukins, cytokines, lymphokines, chemokines, growth factors, ketones, electrolytes, enzymes, medication, and/or other drug levels, and/or levels and/or changes in one or more of these or other substances in the blood plasma, local interstitial fluid, and/or cerebrospinal fluid, may be sensed, using, e.g., one or more Chemically Sensitive Field-Effect Transistors (CHEMFETs) such as Enzyme-Selective Field-Effect Transistors (ENFETs) or Ion-Sensitive Field-Effect Transistors (ISFETs, as are available from Sentron CMT of Enschede, The Netherlands). For example, when electrodes and/or infusion outlet(s) of SCU 130 are implanted in or near the ventrobasal area of the thalamus, a stimulating electrode of SCU 130, or other sensing means contained in electrode lead, catheter, IPG, microstimulator, or any other part of the system may be used to sense changes in neural firing frequency. (As used herein, "adjacent" or "near" means as close as reasonably possible to targeted tissue, including touching or even being positioned within the tissue, but in general, may be as far as about 150 mm from the target tissue.)

Alternatively, an "SCU" dedicated to sensory processes communicates with an SCU providing stimulation pulses. The implant circuitry 170 may, if necessary, amplify and transmit these sensed signals, which may be digital or analog. Other methods of determining the required electrical and/or drug stimulation include measuring impedance, acidity/alkalinity (via a pH sensor), muscle activity (e.g., limb EMG), nerve activity (e.g., ENG), acceleration (e.g., via accelerometer), or other activity other methods mentioned herein, and others that will be evident to those of skill in the field upon review of the present disclosure. The sensed information may be used to control stimulation parameters in a closed-loop manner.

For instance, in several embodiments of the present invention, a first and second "SCU" are provided. The second "SCU" periodically (e.g. once per minute) records EEG activity (or the level of some substance, etc.), which it transmits to the first SCU. The first SCU uses the sensed information to adjust electrical and/or drug stimulation parameters according to an algorithm programmed, e.g., by a physician. For example, the amplitude and/or frequency of electrical stimulation may be increased in response to increased EEG activity. In some alternatives, one SCU performs both the sensing and stimulating functions, as discussed in more detail presently.

While an SCU 130 may also incorporate means of sensing symptoms or other prognostic or diagnostic indicators of pain, e.g., via levels of a neurotransmitter or hormone, it may alternatively or additionally be desirable to use a separate or specialized implantable device to record and telemeter physiological conditions/responses in order to adjust electrical stimulation and/or drug infusion parameters. This information may be transmitted to an external device, such as external appliance 220, or may be transmitted directly to implanted SCU(s) 130. However, in some cases, it may not be necessary or desired to include a sensing function or device, in which case stimulation parameters are determined and refined, for instance, by patient feedback, or the like.

Thus, it is seen that in accordance with the present invention, one or more external appliances may be provided to interact with SCU 130, and may be used to accomplish, potentially among other things, one or more of the following functions:

Function 1: If necessary, transmit electrical power from the external electronic appliance 230 via appliance 220 to SCU 130 in order to power the device and/or recharge the power source/storage device 180. External electronic appliance 230 may include an automatic algorithm that adjusts electrical and/or drug stimulation parameters automatically whenever the SCU(s) 130 is/are recharged.

Function 2: Transmit data from the external appliance 230 via the external appliance 220 to SCU 130 in order to change the parameters of electrical and/or drug stimulation used by SCU 130.

Function 3: Transmit sensed data indicating a need for treatment or in response to stimulation from SCU 130 (e.g., electrical activity of a neural population (via EEG), neurotransmitter levels, levels of neurotransmitter breakdown products, medication levels, hormone levels, or other activity) to external appliance 230 via external appliance 220.

Function 4: Transmit data indicating state of the SCU 130 (e.g., battery level, drug level, stimulation parameters, etc.) to external appliance 230 via external appliance 220.

By way of example, a treatment modality for chronic pain may be carried out according to the following sequence of procedures:

1. An SCU 130 is implanted so that its electrodes 152 and/or infusion outlet 162 are located in or near the ventrobasal area of the thalamus. If necessary or desired, electrodes 152' and/or outlets 162' may additionally or alternatively be located in or near the PVG and/or PAG.
2. Using Function 2 described above (i.e., transmitting data) of external electronic appliance 230 and external appliance 220, SCU 130 is commanded to produce a series of inhibitory electrical stimulation pulses, possibly with gradually increasing amplitude, and possibly while infusing gradually increasing amounts of an inhibitory transmitter, e.g., GABA.
3. After each stimulation pulse, series of pulses, or at some other predefined interval, any change in, e.g., electrical activity of a neural population (e.g., EEG) resulting from the electrical and/or drug stimulation is sensed, for instance, by one or more electrodes 152, 152' or sensors of a second SCU 130, such as a microstimulator SCU 130. These responses are converted to data and telemetered out to external electronic appliance 230 via Function 3.
4. From the response data received at external appliance 230 from SCU 130, or from other assessment, the stimulus threshold for obtaining a response is determined and is used by a clinician 242 acting directly 238 or by other computing means 248 to transmit the desired electrical and/or drug stimulation parameters to SCU 130 in accordance with Function 2.
5. When patient 200 desires to invoke electrical stimulation and/or drug infusion, patient 200 employs controller 210 to set SCU 130 in a state where it delivers a prescribed stimulation pattern from a predetermined range of allowable stimulation patterns.
6. To cease electrical and/or drug stimulation, patient 200 employs controller 210 to turn off SCU 130.
7. Periodically, the patient or caregiver recharges the power source/storage device 180 of SCU 130, if necessary, in accordance with Function 1 described above (i.e., transmit electrical power).

For the treatment of any of the various severities, locations, and types of pain, it may be desirable to modify or adjust the algorithmic functions performed by the implanted and/or external components, as well as the surgical approaches, in ways that would be obvious to skilled practitioners of these arts. For example, in some situations, it may be desirable to employ more than one SCU 130, each of which could be separately controlled by means of a digital address. Multiple channels and/or multiple patterns of electrical and/or drug stimulation might thereby be programmed by the clinician and controlled by the patient in order to, for instance, deal with complex or multiple symptoms or conditions, such as multiple pain syndromes.

In some embodiments discussed earlier, SCU 130, or a group of two or more SCUs, is controlled via closed-loop operation. A need for and/or response to stimulation is sensed via SCU 130, or by an additional SCU (which may or may not be dedicated to the sensing function), or by another implanted or external device. If necessary, the sensed information is transmitted to SCU 130. In some cases, the sensing and stimulating are performed by one SCU. In some embodiments, the parameters used by SCU 130 are automatically adjusted based on the sensed information. Thus, the electrical and/or drug stimulation parameters are adjusted in a closed-loop manner to provide stimulation tailored to the need for and/or response to the electrical and/or drug stimulation.

Figure 9:
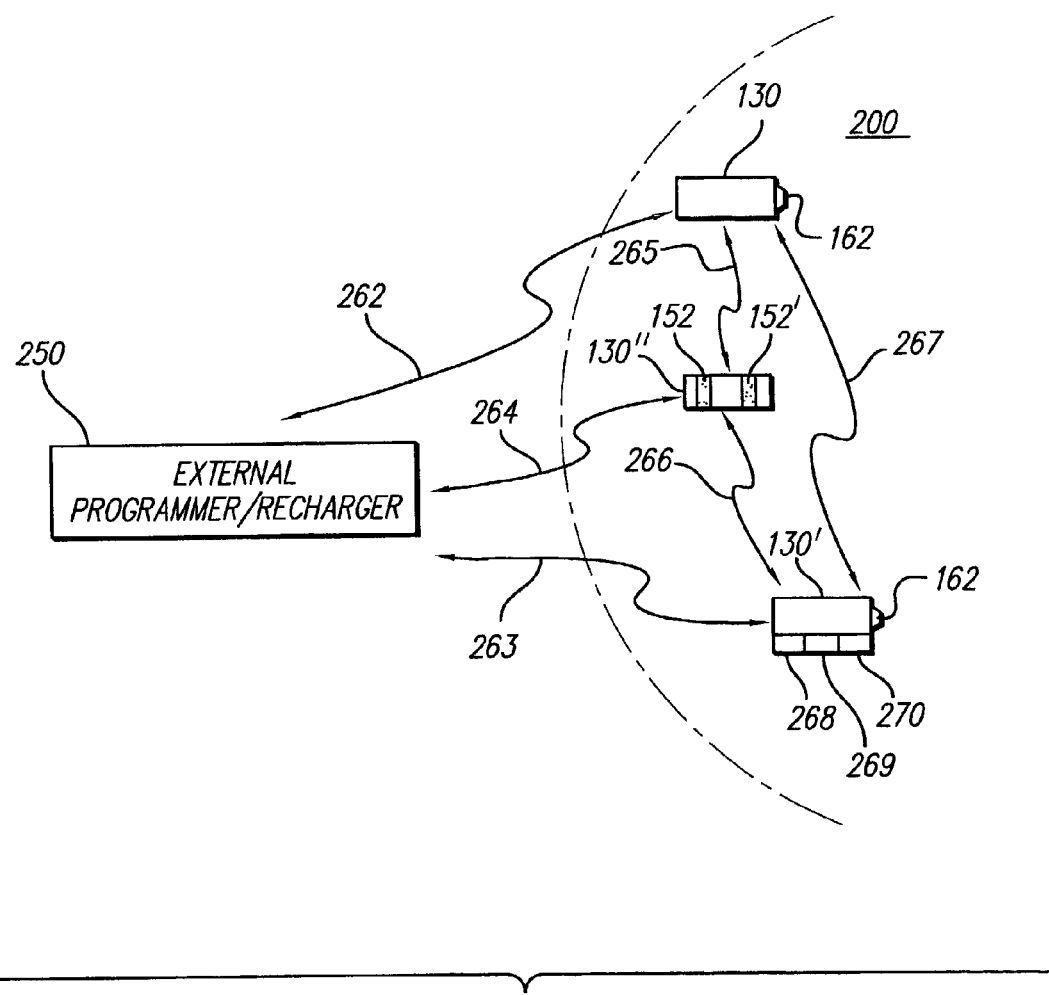
FIG. 9 depicts a system of implantable devices that communicate with each other and/or with external control/programming devices.

For instance, as shown in the example of FIG. 9, a first SCU 130, implanted beneath the skin of the patient 200, provides a first medication or substance; a second SCU 130' provides a second medication or substance; and a third SCU 130" provides electrical stimulation via electrodes 152 and 152'. As mentioned earlier, the implanted devices may operate independently or may operate in a coordinated manner with other similar implanted devices, other implanted devices, or other devices external to the patient's body, as shown by the control lines 262, 263 and 264 in FIG. 9. That is, in accordance with certain embodiments of the invention, the external controller 250 controls the operation of each of the implanted devices 130, 130' and 130".

According to various embodiments of the invention, an implanted device, e.g. SCU 130, may control or operate under the control of another implanted device(s), e.g., SCU 130' and/or SCU 130". That is, a device made in accordance with the invention may communicate with other implanted stimulators, other implanted devices, and/or devices external to a patient's body, e.g., via an RF link, an ultrasonic link, a thermal link, an optical link, or the like. Specifically, as illustrated in FIG. 9, SCU 130, 130', and/or 130", made in accordance with the invention, may communicate with an external remote control (e.g., patient and/or physician programmer 250) that is capable of sending commands and/or data to implanted devices and that may also be capable of receiving commands and/or data from implanted devices.

A drug infusion stimulator made in accordance with the invention may incorporate communication means for communicating with one or more external or site-specific drug delivery devices, and, further, may have the control flexibility to synchronize and control the duration of drug delivery. The associated drug delivery device typically provides a feedback signal that lets the control device know it has received and understood commands. The communication signal between the implanted stimulator and the drug delivery device may be encoded to prevent the accidental or inadvertent delivery of drugs by other signals.

An SCU made in accordance with the invention thus incorporates, in some embodiments, first sensing means 268 for sensing therapeutic effects, clinical variables, or other indicators of the state of the patient, such as EEG, impedance, pH, EMG, ENG, and/or acceleration. The stimulator additionally or alternatively incorporates second means 269 for sensing neurotransmitter levels and/or their associated breakdown product levels, medication levels and/or other drug levels, hormone, enzyme, ketone, electrolytes, interleukin, cytokine, lymphokine, chemokine, and/or growth factor levels and/or changes in one or more of these or other substances in the blood plasma, local interstitial fluid, and/or cerebrospinal fluid. The stimulator additionally or alternatively incorporates third means 270 for sensing electrical current levels and/or waveforms supplied by another source of electrical energy. Sensed information may be used to control infusion and/or electrical parameters in a closed loop manner, as shown by control lines 266, 267, and 265. Thus, the sensing means may be incorporated into a device that also includes electrical and/or drug stimulation, or the sensing means (that may or may not have stimulating means), may communicate the sensed information to another device (s) with stimulating means.

According to some embodiments of the invention, the electrical and/or drug stimulation decreases activity of one or more of those areas of the brain that exhibit chronic increased activity in patients experiencing pain relative to control subjects. Such inhibitory stimulation is likely to be produced by relatively high-frequency electrical stimulation (e.g., greater than about 100–150 Hz), an excitatory neurotransmitter antagonist(s) (e.g., the NMDA receptor antagonist, MK801), an inhibitory neurotransmitter agonist (s) (e.g., diazepam), an agonist thereof, an agent that increases the level of an inhibitory neurotransmitter, an agent that decreases the level of an excitatory neurotransmitter, a local anesthetic agent (e.g., lidocaine), and/or an analgesic medication (e.g., an opiate). This stimulation may be applied to one or more of the ventrobasal (VB) area of the thalamus, including the ventral posteromedial (VPM) nucleus 100 and the ventral posterolateral (VPL) nucleus 104, the posterior complex of the thalamus (PO) 108, the ventrolateral nucleus of the thalamus (VL) 112, and/or the sensory cortex 117 to treat pain.

According to other embodiments of the invention, the electrical and/or drug stimulation increases activity of one or more of those areas of the brain that exhibit chronic decreased activity in patients experiencing pain relative to control subjects. Such excitatory stimulation is likely to be produced by relatively low-frequency electrical stimulation (e.g., less than about 50–100 Hz), an excitatory neurotransmitter agonist(s) (e.g., bethanechol, norepinephrine), an agonist thereof, an inhibitory neurotransmitter antagonist(s) (e.g., bicuculline), an agent that increases the level of an excitatory neurotransmitter (e.g., edrophonium), an agent that decreases the level of an inhibitory neurotransmitter, and/or an analgesic medication (e.g., an opiate). (Opiates are excitatory in some locations and circumstances, and are inhibitory in other locations and circumstances.) This stimulation may also/instead be applied to one or more of the motor cortex 116, the cingulate gyrus 118, the internal capsule 120, the medial lemniscus 122, the periventricular grey (PVG) matter 124, and/or the periaqueductal grey (PAG) matter 126 to treat pain.

In various embodiments, sensing means described earlier may be used to orchestrate first the activation of SCU(s) targeting one or more areas of the brain, and then, when appropriate, SCU(s) targeting another area(s) and/or by different means. Alternatively, this orchestration may be programmed, and not based on a sensed condition.

While the invention herein disclosed has been described by means of specific embodiments and applications thereof, numerous modifications and variations could be made thereto by those skilled in the art without departing from the scope of the invention set forth in the claims.

What is claimed is:

1. A method of treating patients with pain, comprising:
    implanting at least one system control unit including at least one infusion outlet in at least one of the skull and the brain of the patient, wherein the at least one unit controls the delivery of at least one stimulating drug through the at least one outlet to at least one area of the brain affecting pain;
    applying the at least one stimulating drug to the at least one area of the brain in order to at least in part alleviate the pain of the patient being treated;
    wherein the area of the brain is selected from at least one of the ventrobasal (VB) area of the thalamus, the ventral posteromedial (VPM) nucleus, the ventral posterolateral nucleus (VPL), the ventrolateral nucleus (VL), the posterior complex of the thalamus (PO), the motor cortex, the sensory cortex, the cingulate gyrus, the medial lemniscus, the internal capsule, the periventricular grey (PVG) matter, and the periaqueductal grey (PAG) matter.

2. The method of claim 1 wherein the at least one stimulating drug increases excitement of at least one area of the brain affecting pain that exhibits chronic decreased activity.

3. The method of claim 2 wherein the at least one stimulating drug is applied to at least one of the motor cortex, the cingulate gyrus, the medial lemniscus, the internal capsule, the periventricular grey (PVG) matter, and the periaqueductal grey (PAG) matter.

4. The method of claim 2 wherein the stimulating drug is at least one of an excitatory neurotransmitter agonist, an inhibitory neurotransmitter antagonist, an agent that increases the level of an excitatory neurotransmitter, and an agent that decreases the level of an inhibitory neurotransmitter, and an analgesic medication.

5. The method of treatment of claim 2 wherein the system control unit is connected to at least two electrodes, and wherein the method further comprises delivering electrical stimulation via the at least two electrodes, and wherein the electrical stimulation is delivered at a frequency less than about 100 Hz.

6. The method of claim 1 wherein the at least one stimulating drug decreases excitement of at least one area of the brain affecting pain that exhibits chronic increased activity.

7. The method of claim 6 wherein the at least one stimulating drug is applied to at least one of the ventrobasal (VB) area of the thalamus, the ventral posteromedial (VPM) nucleus, the ventral posterolateral nucleus (VPL), the ventrolateral nucleus (VL), the sensory cortex, and the posterior complex of the thalamus (PO).

8. The method of claim 6 wherein the stimulating drug is at least one of an excitatory neurotransmitter antagonist, an inhibitory neurotransmitter agonist, an agent that increases the level of an inhibitory neurotransmitter, an agent that decreases the level of an excitatory neurotransmitter, and a local anesthetic agent, and an analgesic medication.

9. The method of claim 8 wherein the stimulating drug is at least one of MK801, an agonist thereof, and an opiate.

10. The method of treatment of claim 6 wherein the system control unit is connected to at least two electrodes, and wherein the method further comprises delivering electrical stimulation via the at least two electrodes, and wherein the electrical stimulation is delivered at a frequency greater than about 100 Hz.

11. The method of treatment of claim 1 wherein the system control unit is connected to at least two electrodes, and wherein the method further comprises delivering electrical stimulation via the at least two electrodes.

12. The method of claim 1 further comprising sensing at least one condition and using the at least one sensed condition to automatically determine the stimulus to apply.

13. The method of claim 12 wherein the at least one sensed condition is at least one of electrical activity of a neural population, impedance, pH, muscle activity, neural activity, acceleration, a neurotransmitter level, change in a neurotransmitter level, a neurotransmitter breakdown product level, change in a neurotransmitter breakdown product level, a medication level, change in a medication level, a drug level, change in a drug level, a hormone level, change in a hormone level, an interleukin level, change in an interleukin level, a cytokine level, change in a cytokine level, a lymphokine level, change in a lymphokine level, a chemokine level, change in a chemokine level, a growth factor level, change in a growth factor level, an enzyme level, change in an enzyme level, a ketone level, change in a ketone level, an electrolyte level, change in an electrolyte level, level of a substance in the blood plasma, change in level of a substance in the blood plasma, level of a substance in the local interstitial fluid, change in level of a substance in the local interstitial fluid, level of a substance in the cerebrospinal fluid, and change in level of a substance in the cerebrospinal fluid.

14. A method of treating patients with pain, comprising; implanting at least one system control unit in at least one of the skull and the brain of the patient, wherein the at least one unit controls the delivery of at least one stimulus to at least one area of the brain affecting pain;

applying the at least one stimulus to the at least one area of the brain in order to at least in part alleviate the pain of the patient being treated; and sensing at least one condition and using the at least one sensed condition to automatically determine the stimulus to apply;

wherein the system control unit is connected to at least one infusion outlet and at least two electrodes, and wherein the method further comprises delivering at least one stimulating drug through the at least one outlet and delivering electrical stimulation via the at least two electrodes.

15. The method of claim 14 wherein the at least one sensed condition is at least one of electrical activity of a neural population, impedance, pH, muscle activity, neural activity, acceleration, a neurotransmitter level, change in a neurotransmitter level, a neurotransmitter breakdown product level, change in a neurotransmitter breakdown product level, a medication level, change in a medication level, a drug level, change in a drug level, a hormone level, change in a hormone level, an interleukin level, change in an interleukin level, a cytokine level, change in a cytokine level, a lymphokine level, change in a lymphokine level, a chemokine level, change in a chemokine level, a growth factor level, change in a growth factor level, an enzyme level, change in an enzyme level, a ketone level, change in a ketone level, an electrolyte level, change in an electrolyte level, level of a substance in the blood plasma, change in level of a substance in the blood plasma, level of a substance in the local interstitial fluid, change in level of a substance in the local interstitial fluid, level of a substance in the cerebrospinal fluid, and change in level of a substance in the cerebrospinal fluid.

16. The method of claim 14 wherein the at least one area of the brain is selected from at least one of the ventrobasal (VB) area of the thalamus, the ventral posteromedial (VPM) nucleus, the ventral posterolateral nucleus (VPL), the ventrolateral nucleus (VL), the posterior complex of the thalamus (PO), the motor cortex, the sensory cortex, the cingulate gyrus, the medial lemniscus, the internal capsule, the periventricular grey (PVG) matter, and the periaqueductal grey (PAG) matter.

17. The method of claim 14 wherein the system control unit is connected to at least one infusion outlet, and wherein the method further comprises delivering at least one stimulation drug through the at least one outlet.

18. The method of claim 14 wherein the system control unit is connected to at least two electrodes, and wherein the method further comprises delivering electrical stimulation via the at least two electrodes.

19. A method of treating patients with pain, comprising:
implanting at least one system control unit in at least one of the skull and the brain of the patient, wherein the at least one unit controls the delivery of at least one stimulus to at least one area of the brain affecting pain;

applying the at least one stimulus to the at least one area of the brain in order to at least in part alleviate the pain of the patient being treated; and sensing at least one condition and using the at least one sensed condition to automatically determine the stimulus to apply;

wherein the stimulation increases excitement of at least one area of the brain affecting pain that exhibits chronic decreased activity.

20. The method of claim 19 wherein the stimulation is applied to at least one of the motor cortex, the cingulate gyrus, the medial lemniscus, the internal capsule, the periventricular grey (PVG) matter, and the periaqueductal grey (PAG) matter.

21. The method of claim 19 wherein the stimulation is provided by at least one stimulating drug and wherein the at least one stimulating drug is at least one of an excitatory neurotransmitter agonist, an inhibitory neurotransmitter antagonist, an agent that increases the level of an excitatory neurotransmitter, an agent that decreases the level of an inhibitory neurotransmitter, and an analgesic medication.

22. The method of claim 19 wherein the stimulation is electrical stimulation delivered at a frequency less than about 100 Hz.

23. A method of treating patients with pain, comprising:
   implanting at least one system control unit in at least one of the skull and the brain of the patient, wherein the at least one unit controls the delivery of at least one stimulus to at least one area of the brain affecting pain;
   applying the at least one stimulus to the at least one area of the brain in order to at least in part alleviate the pain of the patient being treated; and
   sensing at least one condition and using the at least one sensed condition to automatically determine the stimulus to apply;
   wherein the stimulation decreases excitement of at least one area of the brain affecting pain that exhibits chronic increased activity.

24. The method of claim 23 wherein the stimulation is applied to at least one of the ventrobasal (VB) area of the thalamus, the ventral posteromedial (VPM) nucleus, the ventral posterolateral nucleus (VPL), the ventrolateral nucleus (VL), the sensory cortex, and the posterior complex of the thalamus (PO).

25. The method of claim 23 wherein the stimulation is provided by at least one stimulating drug and wherein the at least one stimulating drug is at least one of an excitatory neurotransmitter antagonist, an inhibitory neurotransmitter agonist, an agent that increases the level of an inhibitory neurotransmitter, an agent that decreases the level of an excitatory neurotransmitter, a local anesthetic agent, and an analgesic medication.

26. The method of claim 25 wherein the drug is at least one of MK801, an agonist thereof, and an opiate.

27. The method of claim 23 wherein the stimulation is electrical stimulation delivered at a frequency greater than about 100 Hz.

28. A system for treating patients with pain, comprising:
   at least one system control unit configured for implantation entirely within at least one of a brain and a skull;
   at least one of a) a pump coupled to an infusion outlet and b) at least two stimulating electrodes;
   means for operably connecting the at least one system control unit to at least one of the infusion outlet and the electrodes;
   means for providing operating power to the at least one system control unit;
   means for providing stimulation parameters to the at least one system control unit; and
   means for generating stimulation pulses in accordance with the stimulation parameters;
   wherein the pump and infusion outlet and the electrodes are configured to deliver the stimulation pulses through at least one of the infusion outlet and the electrodes to at least one area of the brain affecting pain.

29. The system of claim 28 wherein the system control unit is configured to conform to the profile of the skull.

30. The system of claim 28 wherein the system control unit is a microstimulator implanted entirely within the brain.

31. The system of claim 28 further comprising means for sensing at least one condition indicating a need for treatment for pain.

32. The system of claim 31 further comprising means for using the at least one sensed condition to automatically determine the stimulus to apply.

* * * * *